United States Patent
Sunshine et al.

(10) Patent No.: US 6,741,740 B2
(45) Date of Patent: *May 25, 2004

(54) METHOD FOR SELECTING REPRESENTATIVE ENDMEMBER COMPONENTS FROM SPECTRAL DATA

(75) Inventors: Jessica Miriam Sunshine, Potomac, MD (US); Stefanie Tompkins, Centreville, VA (US); Kellie Sue McNaron-Brown, Centreville, VA (US)

(73) Assignee: Science Applications International Corporation, San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/387,867

(22) Filed: Mar. 14, 2003

(65) Prior Publication Data

US 2003/0161533 A1 Aug. 28, 2003

Related U.S. Application Data

(63) Continuation of application No. 09/901,680, filed on Jul. 11, 2001.

(51) Int. Cl.[7] .............................. G06K 9/46; G06K 9/62; G06K 9/40
(52) U.S. Cl. ...................... 382/191; 382/225; 382/274
(58) Field of Search ................................ 382/190, 191, 382/192, 194, 195, 205, 260, 274, 282, 283, 224, 225, 110; 235/454; 250/334, 347, 348

(56) References Cited

U.S. PATENT DOCUMENTS

| | | | |
|---|---|---|---|
| 6,008,492 A | | 12/1999 | Slater et al. ................. 250/334 |
| 6,075,891 A | * | 6/2000 | Burman ....................... 382/191 |
| 6,608,931 B2 | * | 8/2003 | Sunshine et al. ........... 382/191 |

OTHER PUBLICATIONS

Preliminary Examination Report for application No. PCT/US02/13497, dated Oct. 8, 2003 (mailing date).

Gemmell, et al., "Estimating Forest Cover in a Boreal Forest Test Using Thematic Mapper Data from Two Dates," *Elsevier Science, Inc.*, ISBN: 0034–4257, pp. 197–211, Feb., 2001.

Yi–Hsing Tseng, "Spectral Mixture Analysis of Hyperspectral Data," *GIS Development, Asian Conference in Remote Sensing*, 13 pp., Nov. 1999.

ENVI Tutorial #10, "Advanced Hyperspectral Analysis," 18 pp., 1995 AVIRIS.

K. O. Niemann, David G. Goodenough, Andrew Dyk, A. S. Bhogal, University of Victoria, Pixel Unmixing for Hyperspectral Measurement of Foliar Chemistry in Pacific Northwest Coastal Forests, www.aft.pfc.forestry.ca/igarss99/Pixel_unmixing, Apr. 30, 2001.

Spectral Angle Mapper (SAM), www.phylab.mtu.edu/~tip/remotesensing/tutorial/sam/sam, Apr. 30, 2001.

(List continued on next page.)

*Primary Examiner*—Mehrdad Dastouri
(74) *Attorney, Agent, or Firm*—Kilpatrick Stockton LLP

(57) ABSTRACT

Described herein is a process for objectively and automatically determining spectral endmembers and transforming Spectral Mixture Analysis (SMA) from a widely used research technique into a user-friendly tool that can support the needs of all types of remote sensing. The process extracts endmembers from a spectral dataset using a knowledge-based approach. The process identifies a series of starting spectra that are consistent with a scene and its environment. The process then finds endmembers iteratively, selecting each new endmember based on a combination of physically and statistically-based tests. The tests combine spectral and spatial criteria and decision trees to ensure that the resulting endmembers are physically representative of the scene.

21 Claims, 6 Drawing Sheets

OTHER PUBLICATIONS

Manual Endmember Selection Tool, www.cires.Colorado.edu/cses/research/ems_man, Mar. 22, 2001.

Eugene W. Martin, "Measurement of Impervious Surface Area from Landsat Thematic Mapper Data using Sprectal Mixture Analysis", www.commenspace.org/papers/sma/, Mar. 22, 2001.

"Abacus", www.saic.com/abacus, Feb. 26, 2001.

J. Sunshine, John F. Mustard, Melanie A. Harlow, Andrew Elmore, NASA Earth Science Enterprise Commercial Remote Sensing Program Affiliated Research Center Brown University, Dec. 17, 1999.

Nirmal Keshava, John F. Mustard, "Spectral Unmixing", *IEEE Signal Processing Magazine*, Jan. 2002, p. 44–57.

John B. Adams, Milton O. Smith, Alan R.Gillespie, "Imaging Spectroscopy: Interpretation Based on Spectral Mixture Analysis", *Remote Geochemical Analysis*, Oct. 2, 2002, pp. 145–166.

John F. Mustard, Jessica M. Sunshine, "Spectral Analysis for Earth Science: Investigations Using Remote Sensing Data", *Remote Sensing for the Earth Sciences: Manual of Remote Sensing, 3 ed., vol. 3*, Copyright 1999, pp. 251–306.

J. B. Adams, D. E. Sabol, V. Kapos, R. A. Filho, D. A. Roberts, M. O. Smith, "Classification of Multispectral Images Based on Fractions of Endmembers: Application to Land–Cover Change in the Brazilian Amazon", *Remote Sens. Environment 52:137–154*, 1995.

J. B. Adams, Milton O. Smith, "Spectral Mixture Modeling: A New Analysis of Rock and Soil Types at the Viking Lander 1 Site", *Journal of Geophysical Research, vol. 91, No. 88*, Jul. 10, 1986, pp. 8098–8112.

* cited by examiner-

METHOD FOR SELECTING REPRESENTATIVE ENDMEMBER COMPONENTS FROM SPECTRAL DATA

CROSS-REFERENCE TO RELATED APPLICATIONS

The current application is a continuation application of U.S. application Ser. No. 09/901,680 filed Jul. 11, 2001, and titled Method for Selecting Representative Endmember Components from Septral Data.

BACKGROUND OF THE INVENTION

1. Field of the Invention

The subject matter of the present invention generally involves spectral image analysis. More particularly, the present invention involves processes for determining representative scene components, or endmembers, from spectral imagery.

2. Description of the Related Art

It has long been recognized that at spatial scales typical of remotely sensed data, the surface corresponding to a given pixel is rarely composed of a single physical component, but rather a combination of "sub-pixel" constituents. This mixed-pixel concept was developed into a quantitative model for interpretation of spectral images, Spectral Mixture Analysis ("SMA"). SMA involves an interactive selection and refinement of key components, or endmembers, to achieve an acceptable solution. The SMA model is based on the assumption that remotely sensed spectral measurements are mixed signatures, which vary across the scene as the relative proportion of each component changes. SMA can therefore be used to translate spectral imagery into quantitative maps also referred to as abundance maps, showing the percent cover of each spectrally distinct scene component. The number of endmembers resolvable with SMA is dependent on the complexity of the actual surface, the spatial resolution of the imagery, and the spectral resolution of the data. However, even in hyperspectral imagery of complex regions, SMA is most robust when a few (<10) spectrally distinct components are modeled. For instance, a forested scene would be modeled as a combination of green vegetation (e.g. leaves, grass), non-photosynthetic vegetation (NPV, e.g. bark, wood, dry leaves), soils, and shade. This last component, shade, is unique to SMA. The shade endmember accounts for spectral variations in illumination caused by either topography or sub-pixel surface texture. With SMA, a tree or group of trees can therefore be modeled not by a single "tree" signature, but instead by a combination of green vegetation, NPV, and shade. The selection of these types of endmembers generally requires at least one expert user's input to be successful.

Alternatively, complex statistical and mathematical approaches have been employed in order to perform endmember selection, but none have been shown to provide routine and reliable results. These approaches utilize purely mathematical transformations of the spectral data, without regard for what physical information the data actually represents, e.g., vegetation, NPV, soil, shade, buildings, roads, etc. The endmembers determined through these processes are physically meaningless and not comparable to those derived by expert users. As such, their utility is limited and at best require subsequent subjective interpretation by an expert.

Current endmember selection methods are thus either manual with expert users doing the processing or automatic using signal processing, but with less reliable results that still require expert user interpretation.

SUMMARY OF THE INVENTION

Summary of the Problem

Currently, the process of determining the number and nature of these spectrally distinct components (or "endmembers") using either the manual or statistical selection process is both subjective and labor intensive. Because of this, SMA-based classification, although clearly of significant use in many applications, has largely been limited to labor intensive research projects. In such studies, endmembers are typically selected manually by-experienced analysts. Results from this process are subjective and vary from one investigator to another. Further, as the complexity of data sets increase, so does the time required to perform SMA as does the likelihood of greater error. Consequently, there is a need in the art for a faster, more objective, more cost-effective, user-friendly process for selecting representative spectral endmembers for a scene. As more and more data become available from, e.g., commercial airborne systems and earth observational satellites which include hyperspectral sensors, there is an increasing need for a process that aids both experienced and novice end-users to work more efficiently, significantly reduces costs, and enhances the utility of spectral imagery.

Summary of the Solution

The invention described herein is an objective and automated process for determining spectral endmembers and transforming Spectral Mixture Analysis (SMA) from a widely used research technique into a user-friendly tool that can support the needs of all types of remote sensing. The process extracts endmembers from a spectral dataset using a knowledge-based approach. The process identifies a series of starting spectra that are consistent with a scene and its environment. The process then finds endmembers iteratively, selecting each new endmember based on a combination of physically and statistically-based tests. The tests combine spectral and spatial criteria and decision trees to ensure that the resulting endmembers are representative of the scene.

The invention described herein achieves a significant advancement in the application of SMA. As discussed herein, the process of the present invention successfully implements a number of the manual decision making steps that an analyst performs in doing mixture analysis. However, these steps are ordered in a way that leads to far fewer false steps, fewer refinements of endmember selection, and, minimizes the need to remove entire endmember sets from an analysis sequence. Further, the process of the present invention provides users with sophisticated insight into mixture model methods. This is particularly important when working with, for example, complex scenes or on areas where specific objectives must be met.

As a result of the processes described herein, the time required to exploit spectral image data is dramatically reduced. The process makes information from spectral imagery readily available, and expedites critical decision making. The process automatically determines the subpixel proportions of materials in spectral datasets and transforms these data into readily interpretable information layers that can be imported into, e.g., a geographical information system (GIS) database.

Applications of spectral imaging data can support a diverse range of scientific and business operations. Among these, spectral data offers enormous potential for routinely creating geologic and soil maps, environmental monitoring, aiding forestry and agriculture production, land use/land cover mapping, and various applications in support of civil, military, law enforcement, and intelligence communities. For example, high resolution spectral imaging is used to help winegrowers harvest their crops with more precision. By identifying plant health and maturity, vintners can establish optimum harvest schedules that ultimately yield high quality wine. The same methodology holds true for using spectral imaging data to non-destructively detect bruised fruit in large orchards, and also aiding law enforcement officials in detecting marijuana plants from airborne platforms.

More particularly, an embodiment of the present invention provides a process for determining at least one candidate spectral endmember that represents a group of N spectra. The process of this embodiment comprises: building an initial endmember set composed of at least a first and a second spectrum representing at least a first and a second spectral characteristic expected to be in the group of N spectra; unmixing the N spectra within the group of N spectra to determine what portion, if any, of each of the N spectra match at least one of the at least a first and second spectrum; calculating a first metric value for each of the N spectra, wherein the first metric value accounts for a remaining portion of each of the N spectra not matching the at least a first and second spectrum; defining a metric value range, wherein the N spectra having first metric values within the metric value range are defined as M spectra; ordering the M spectra from highest first metric value to lowest first metric value; comparing each of the M spectra, beginning with the M spectra having the highest first metric value, to each of the N spectra, to determine the frequency with which each of the M spectra occurs within the N spectra; and calculating a second metric value for each of the M spectra, wherein the second metric value combines the frequency of occurrence of each of the M spectra within the N spectra with a first metric value for each of the M spectra, wherein the M spectra having the largest second metric value is the at least one candidate endmember.

A further embodiment of the present invention provides a process for determining at least one candidate spectral endmember that represents a group of N spectra. The process of this embodiment comprises: building an initial endmember set composed of at least a first and a second spectrum representing at least a first and a second spectral characteristic expected to be in the group of N spectra; unmixing the N spectra within the group of spectra to determine what portion, if any, of each of the N spectra match at least one of the at least a first and a second spectrum; defining an error value for each of the N spectra, wherein the error value is the portion of each of the N spectra that does not match a combination of the at least a first and a second spectrum; comparing the error value for each of the N spectra to a predetermined error value range, wherein spectra having error values within the predetermined error value range are defined as M spectra; ordering the M spectra from highest error value to lowest error value; comparing each of the M spectra, beginning with the M spectra having the highest error value, to each of the N spectra, to determine the frequency with which each of the M spectra occurs within the N spectra; and calculating a metric for each of the M spectra, wherein the metric combines the frequency of occurrence of each of the M spectra within the N spectra with an error value for each of the M spectra, wherein the M spectra having the largest metric is the at least one candidate endmember.

A still further embodiment of the present invention provides a process for determining at least one candidate spectral endmember within a scene having N pixels using scene spectral data. This embodiment of the present invention comprises: building a first endmember, wherein the first endmember represents a first spectral characteristic expected to be in the scene; building a second endmember for the scene, wherein the second endmember represents a second spectral characteristic expected to be in the scene; unmixing the N pixels in the scene to determine what portions of each of the N pixels match at least one of the first and second endmembers; defining a remaining portion for each of the N pixels not matching a combination of the first and second endmembers as an error value, wherein each error value corresponds to a residual spectra and the residual spectra in combination form a residual spectrum of the N pixels; calculating a root mean square (RMS) error for the N pixels by combining the error values for the residual spectra; determining an acceptable range of deviation from the mean RMS error; comparing each of the RMS error values for each of the N pixels to the acceptable range of deviation from the mean RMS error and keeping the M pixels that are within the acceptable range of deviation; ordering the M pixels from highest RMS error value to lowest RMS error value; comparing the corresponding residual spectra of the M pixels, beginning with the M pixel having the highest RMS error value, to the residual spectrum comprising the residual spectrum for the N pixels, to determine the frequency with which each of the corresponding residual spectra of the M pixels occurs within the residual spectra for the N pixels; and calculating a weighting factor for each of the M pixels, wherein the M pixel having the largest weighting factor is the at least one candidate endmember.

DESCRIPTION OF THE PREFERRED EMBODIMENTS OF THE PRESENT INVENTION

Figure 1:
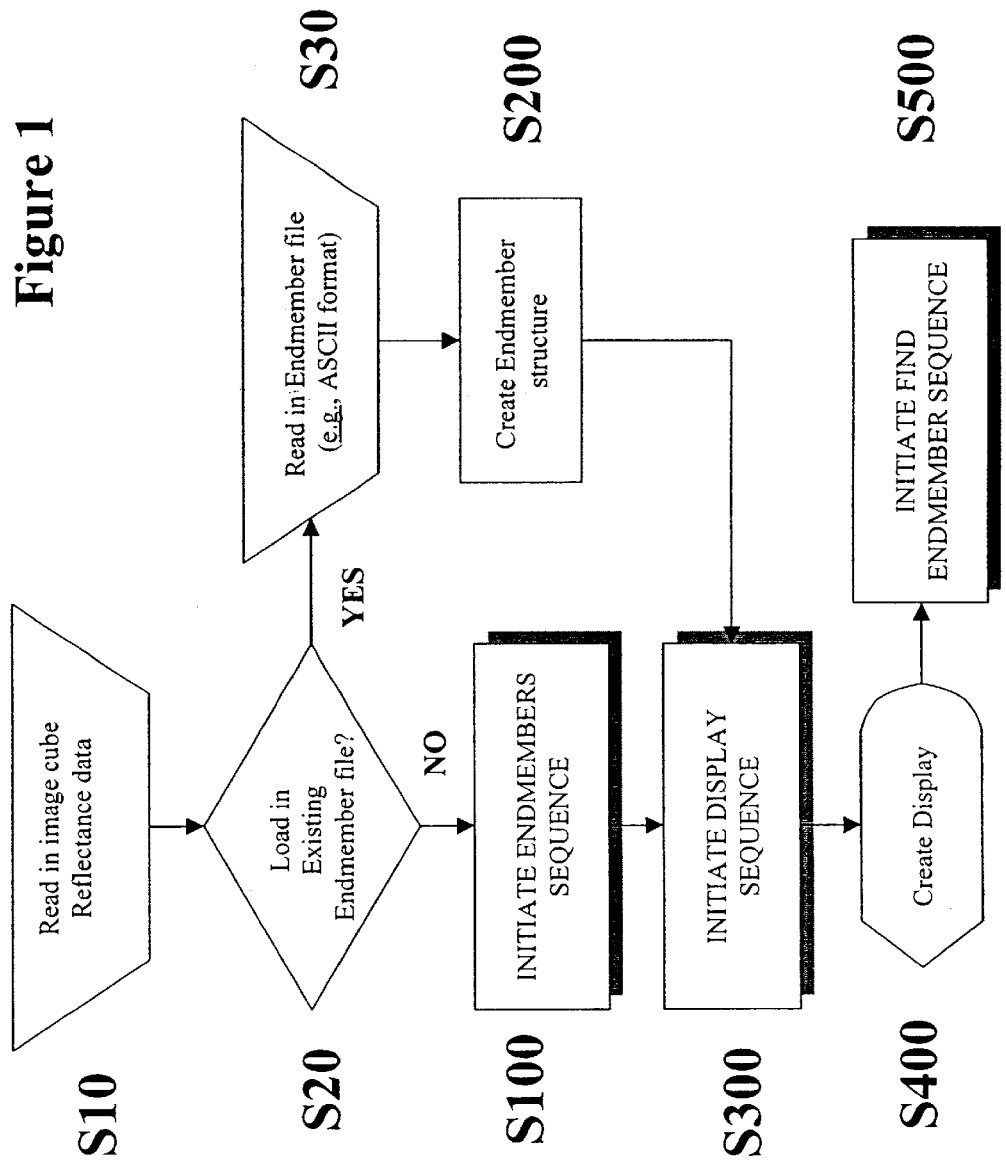
FIG. 1 is a flowchart for finding scene reflectance spectra endmembers according to an embodiment of the present invention.

The following embodiments, though representing the best known mode of practicing the present invention, are not intended to be limited thereto. Based on the knowledge of one skilled in the art, variations of the following embodiments are intended to be part of the scope of the present invention.

The flowchart of FIGS. 1–6 sets forth the general process steps for determining the land cover types, e.g, green vegetation (leaves, grass, etc.), non-photosynthetic vegetation ("NPV") (e.g., bark, wood, dry leaves), soils, snow, ice, roads, buildings, and shade, within a particular scene according to an embodiment of the present invention. Image cube reflectance, emission, or radiance data (hereafter "reflectance data") indicative of a scene is read into a processor S10. The scene boundaries are defined by, for example, a set of ground-based longitudinal and latitudinal coordinates. The reflectance data results from imaging performed by any of a number of sources, such as, satellites, aircraft, weather balloons, in situ or ground based sensors, or the like. One skilled in the art recognizes that the current invention may be used with all types of spectral data, (e.g., multispectral, hyperspectral, ultraspectral) with results varying in level of detail depending on spectral and spatial resolution and spectral range.

As described above, no matter the specifics of the datasets, a spectral measurement in a given pixel is at some scale mixed. For example, even with state of the art remote imagery, in order to identify and classify the land cover types that are represented in the selected scene, it is necessary to determine spectrally distinct components from the combination components received by the imaging system. These spectrally distinct components for a particular scene are referred to as endmembers.

Again, referring to FIG. 1, in an embodiment of the present invention, after the reflectance data for a particular scene is read into the processor S10, pre-existing endmember data for that particular scene is also read into the processor, if available S30. The process of the current invention stores any previously generated endmember data according to location within the scene and the spectrum for each endmember as a function of wavelength. Consequently, after the initial reflectance data is read into the processor S10, the user is queried as to whether the user chooses to load in an existing endmember file for the selected scene S20. If the user chooses to load in an existing endmember file, the file is read into the processor, in for example, ASCII format S30. The endmember data is subjected to a programming subroutine in order to format the data into a recognizable and easily manipulatable endmember data structure S200.

Alternatively, if there is no existing endmember file for the selected scene or the user chooses not to load the existing endmember file, the user initiates an endmember sequence S100 in order to create a new endmember structure. Referring to FIG. 2, after initiating the endmembers sequence S100, a shade spectrum, e.g., 1% percent reflectance spectrum, i.e., unchanging with wavelength, is constructed at the channels for the scene reflectance data S120. In the embodiments described herein, a user assumes that a scene's reflectance data is representative of at least two components, shade or shadow (hereafter "shade") and vegetation. A shade spectrum is constructed in order to take into account and adjust for the presence of inhibiting shade components and can be considered the first endmember. The second endmember is determined from a reference vegetation spectrum that has been read into the processor and resampled using linear interpolation to match the wavelengths of the reflectance scene data set S140. The reference vegetation spectrum is selected from a library of vegetation spectra in an attempt to find a match between known vegetation spectra and scene reflectance data. These preliminary endmembers, i.e., shade and vegetation, are included in the preliminary endmember structure S160 that is outputted at S180 and returning to FIG. 1, is used in a display sequence S300. Alternative embodiments, use various other initial endmember sets, consisting of at least two of the materials expected to be in the scene, based on known data and scene properties. Other materials might include soils, NPV (such as bark, wood and dry leaves), snow, etc., as listed previously.

Figure 3:
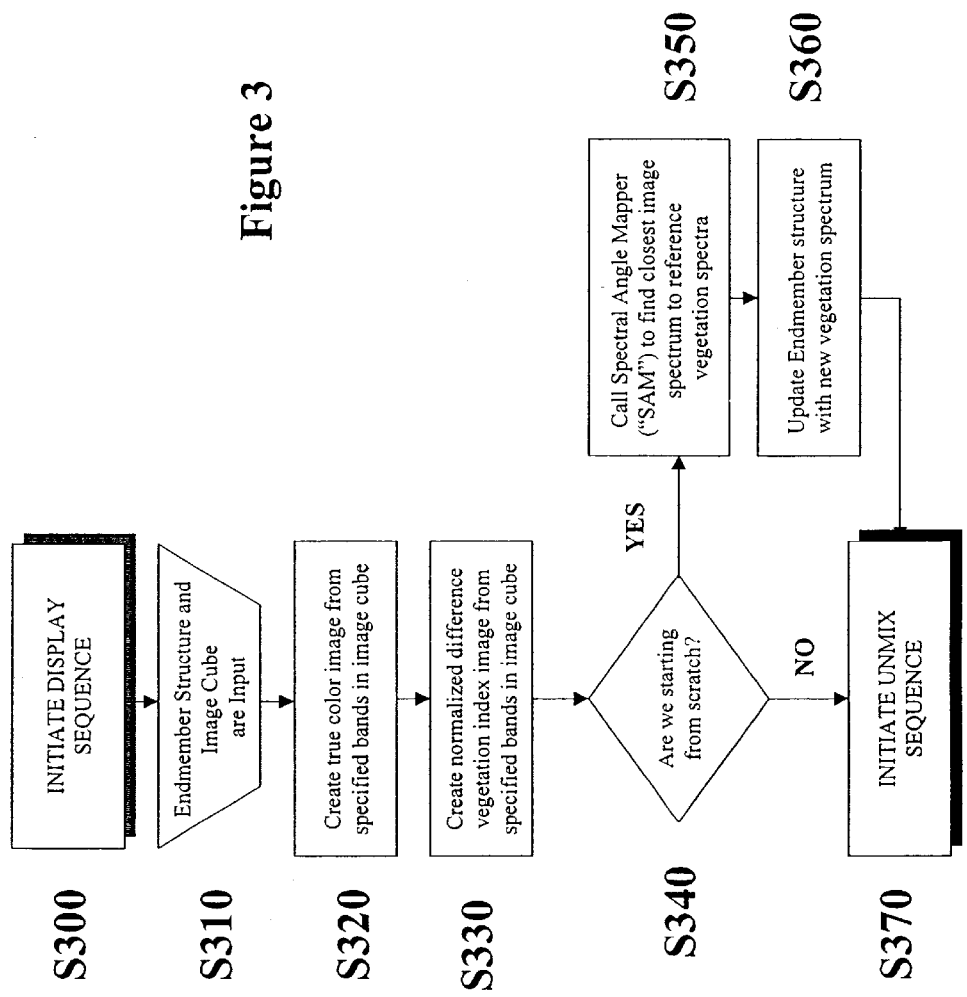
FIG. 3 is a flowchart for initiating a display sequence according to an embodiment of the present invention.

To this point, the process steps described above and the results thereof have been invisible to the user. In order for the user to view results and change parameters accordingly, an embodiment of the present invention facilitates a display of the results. Steps for initiating a display sequence according to an embodiment of the present invention are shown in FIG. 3. The preliminary endmember structure and the scene reflectance data are inputted into a display sequence (e.g., computer program) S310. In order to provide visual aids to the user, an embodiment of the invention provides both a true color image from specified bands in the scene reflectance data S320 and a normalized difference vegetation index ("NDVI") from specified bands in the scene reflectance data S330. NDVI is the traditional vegetation index used by researchers for extracting vegetation abundance from remotely sensed data. It divides the difference between reflectance values in the visible red and near-infrared wavelengths by the overall reflectance in those wavelengths to give an estimate of green vegetation abundance. In essence, the algorithm isolates the dramatic increase in reflectance over the visible red to near infrared wavelengths, and normalizes it by dividing by the overall brightness of each pixel in those wavelengths. Specifically NDVI is:

$$NDVI = \frac{IR - red}{IR + red}$$

The result of this algorithm is a single band data set, ranging from −1 to 1, with values corresponding to photosynthetic vegetation abundance. True color and NDVI images are merely exemplary of the types of images which may be presented to a user during the display sequence. One skilled in the art recognizes the various images which fall within the scope of the invention.

Figure 2:
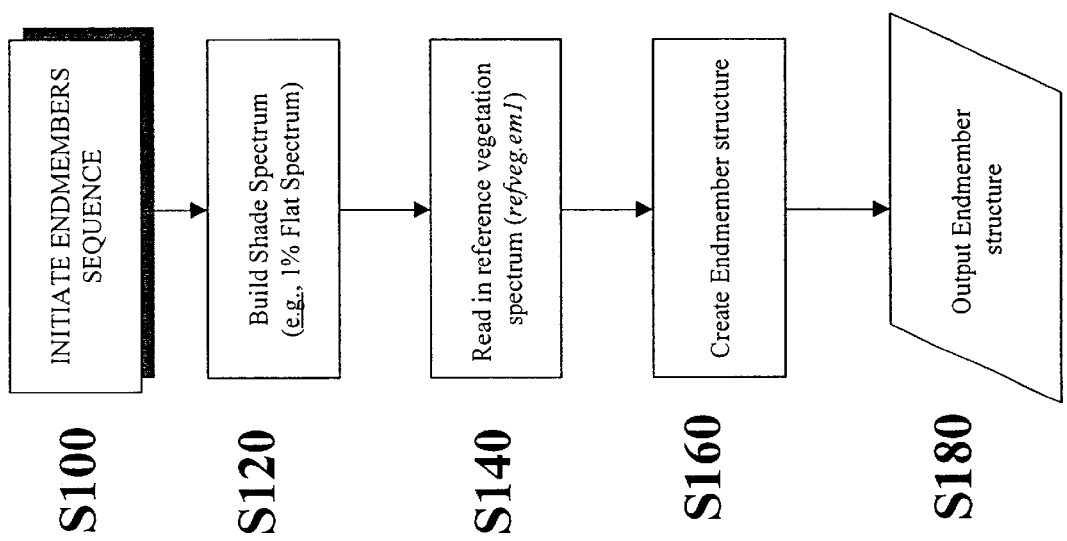
FIG. 2 is a flowchart for initiating an endmember sequence according to an embodiment of the present invention.

Next, similar to steps recited with reference to FIG. 1, the display sequence queries whether or not there is an existing endmember file, or if the sequence must assume that there is no pre-existing information and start from scratch to determine initial endmembers for the scene S340. In the case where there is no pre-existing endmember information, in order to identify initial endmembers, spectral matching algorithms such as Spectral Angle Mapper ("SAM"), or the like, are used to find the closest image spectrum in the scene reflectance data to reference vegetation spectra S350. In order to ascertain the closest spectral signature to specified bands of the scene reflectance data, SAM measures the similarity between an unknown spectrum and the reference spectrum. SAM treats two spectra as two vectors in n-dimension space, where the dimensionality equals the number of bands. The similarity of two spectra (e.g., vectors) will be based on the angle of separation between the two vectors. The smaller angles represent closer matches to the reference spectrum. After running the scene reflectance data through a matching program, such as SAM, the outputted endmember structure from S180 is updated to include the new vegetation spectrum data S360 and a spectral unmixing sequence is initiated S370.

Figure 4:
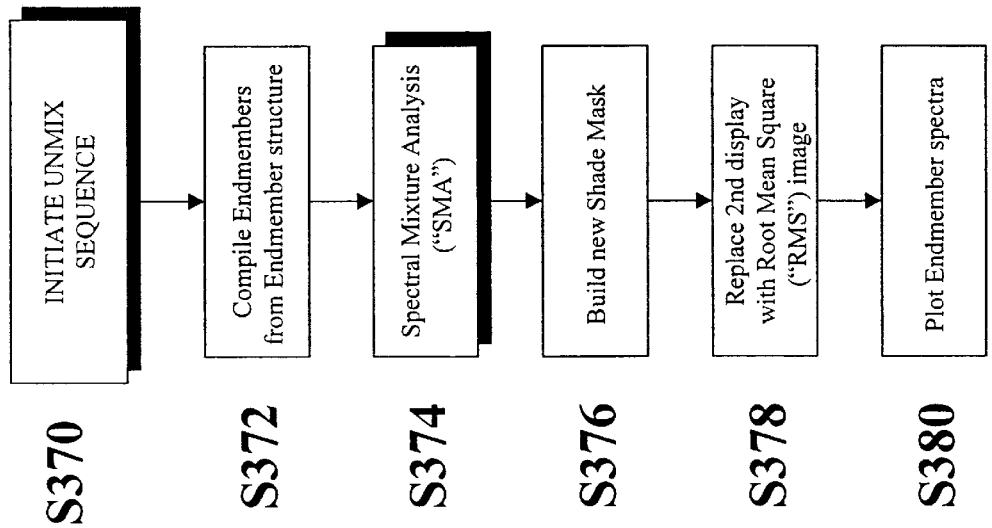
FIG. 4 is a flowchart for initiating an unmixing sequence according to an embodiment of the present invention.

Referring to FIG. 4, after initiating the unmixing sequence S370, endmembers are compiled from the updated endmember structure S372 and spectral mixture analysis is performed on the compiled endmembers S374. The technique of pixel unmixing as it is generally applied assumes a linear model to separate the primary scene components, termed endmembers. Alternatively, non-linear models are applied. The technique relies on the analyst to identify the spectra of the endmembers. These spectra are then typically used in a least-squares inversion to estimate the contribution of each endmember for each pixel by simultaneously solving the following equations for each wavelength b:

$$R_b = \sum_{i=1}^{m} f_i r_{ib} + E_b$$

$$\sum_{i=1}^{m} f_i = 1.0$$

$R_b$=input pixel spectrum at wavelength b
$f_i$=contribution or fractional abundance of the ith endmember
$r_{ib}$=spectrum of the ith endmember
$E_b$=a residual error at wavelength b The model is that $R_b$ is equal to the sum over the number of endmember of $(f_i)(r_{ib})$ plus $E_b$. Variable $r_{ib}$ is the endmember; $f_i$ is the abundance of the end member i; $R_b$ is the pixel spectrum for each end member at band b; and $E_b$ is the residual error at each band b. A second constraint, that the sum of $f_i$ will equal unity (1.0), may also be applied. The results of applying this analysis are a series of images, one for each endmember, containing the percentage, or fractional abundance, of the endmember in each pixel. The collection of abundance images for all endmembers are often referred to as fraction cubes.

Depending on the results of the SMA step, a shade mask is built and applied to the unmixed pixels, e.g., all pixels with greater than a user selection percentage of shade, e.g., 80% shade are masked out S376. Next a root mean square ("RMS") error image is generated and it replaces the NDVI image that is viewable by the user S378. The RMS error image is an image displaying the square root of the sum of the squares of the error as a function of wavelength for each pixel. In an embodiment of the present invention, the RMS error image is an intensity image where bright pixels are areas that are not well defined by the current choice of endmembers, i.e., shade and initial vegetation. The endmember spectra are also plotted in a graph, wherein, for example, the x-axis is wavelength and the y-axis is reflectance S380. At any point after initiating the display sequence S300, the created and updated images and plots are viewable through display S400.

Using the display, the user is able to visualize the images and plots in order to determine how to vary the parameters, e.g., shade threshold, SAM threshold, RMS minimum and maximum (described below), in order to find the next endmember spectrum. The shade threshold parameter adjusts how many dark pixels to allow in the analysis. The value is based on the abundance value of the "shade" endmember. Areas in the "shade" abundance image that are greater than or equal to this value are masked out and are not considered as possible endmembers. The display S400 allows the user to view how the shade threshold constraint affects the spatial analysis of the image by displaying a Shade Mask window. Changing the SAM threshold parameter affects how many pixels in the image are flagged as spectrally similar to the spectrum of the new candidate endmember. The display S400 allows the user to view how this constraint affects the spatial analysis of the image when the colored mask is displayed over the RMS error image. When starting a new image, this parameter is initially a small value (e.g., the default starting value is 0.1). As each new consecutive endmember is found, this value is increased to loosen the matching constraint. Before accepting any new endmember, the user defines the fine balance between spectral uniqueness of each endmember versus the spatial extent of that endmember.

The RMS minimum and maximum establish how many candidate pixels in the image are considered for the next endmember. These two values are the number of standard deviations from the mean RMS error value of the image. A user can find out how many pixels are in the established range and can examine the data to determine the best "RMS Min/Max Sigma" values (discussed further below), through the interactive display S400 via a "Plot RMS Error" button. A window with a histogram plot of the RMS errors of every pixel in the image is shown on the display. The histogram is labeled with a legend to indicate mean RMS error value of the image and indicate the number of candidate spectra listed. The candidate number is the sum of the RMS error values between the two appropriately marked min/max sigma values from the mean.

Figure 5:
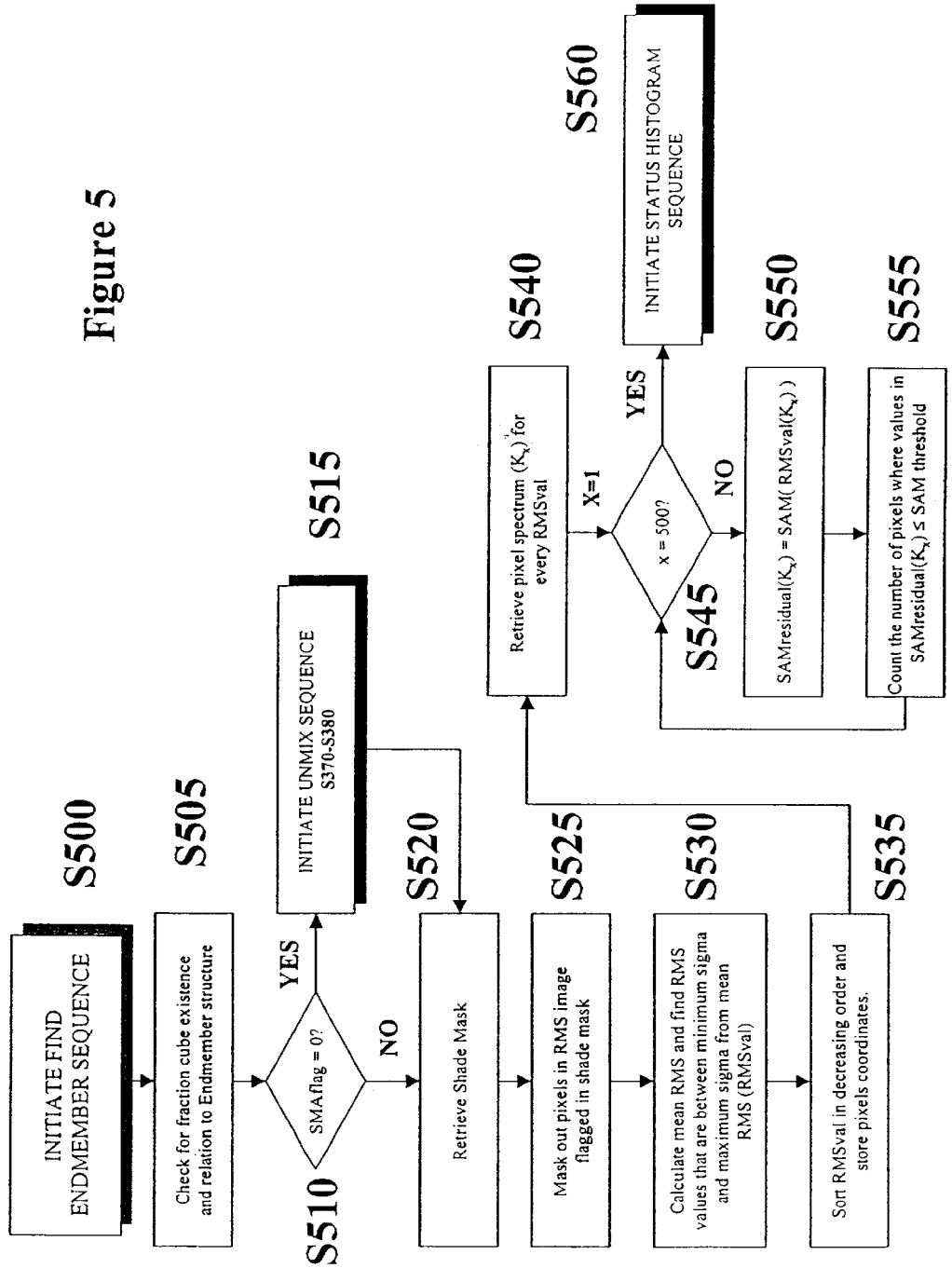
FIG. 5 is a flowchart for initiating a sequence for finding endmembers according to an embodiment of the present invention.

After initiating the display and unmixing sequences as discussed above, the user initiates the find endmember sequence S500. Referring to FIG. 5, the updated endmember structure is compared to any existing fraction cube data to determine if a corresponding unmixing has previously been performed, e.g. at S370–380, S505. If not, i.e., SMAflag=0, then the unmixing sequence is performed S515. Once fraction cube data that corresponds to the endmember structure is in hand, the shade mask is retrieved S520 and pixels in the RMS image that are flagged in the shade mask are masked out from the endmember sequence S525. The pixels remaining after being compared to the shade mask at S525 are subjected to an RMS calculation to determine the mean RMS value at S530. The individual RMS calculations for each pixel are next compared to a user defined RMS range of minimum and maximum from the mean RMS values S530. The pixels having RMS values (RMSval) falling within this range are sorted in decreasing order, e.g., from highest to lowest error, and are stored according to the coordinates of the corresponding pixel S535.

Next, the corresponding residual spectrum ($K_x$) for each RMSval is retrieved S540. More particularly, the residual spectrum is the residual error as a function of wavelength for each pixel in the scene. Each $K_x$, beginning with $K_1$, corresponding to the highest error, is compared to the residual spectrum for every pixel in the image to determine the number of pixels within the image that are similar to $K_1$. Depending on the number of pixels in the image as well as processing limitations, the user selects a predetermined number of $K_x$'s which are evaluated before the endmember determination sequence continues. For example, in S545, x=500 before a histogram sequence is initiated S560. Consequently, 500 RMSvals are evaluated before the histogram is constructed. The evaluation of each RMSval requires comparing each $K_x$ for each RMSval using a matching algorithm, e.g., SAM (as described above) with the residual spectrum for each pixel in the scene, i.e., SAMresidual($K_x$)=SAM(RMSval($K_x$)) S550 and counting the number of pixels in the scene containing the RMSval according to a pre-established threshold for the SAM value, i.e., SAMresidual($K_x$)≦SAM threshold S555.

Figure 6:
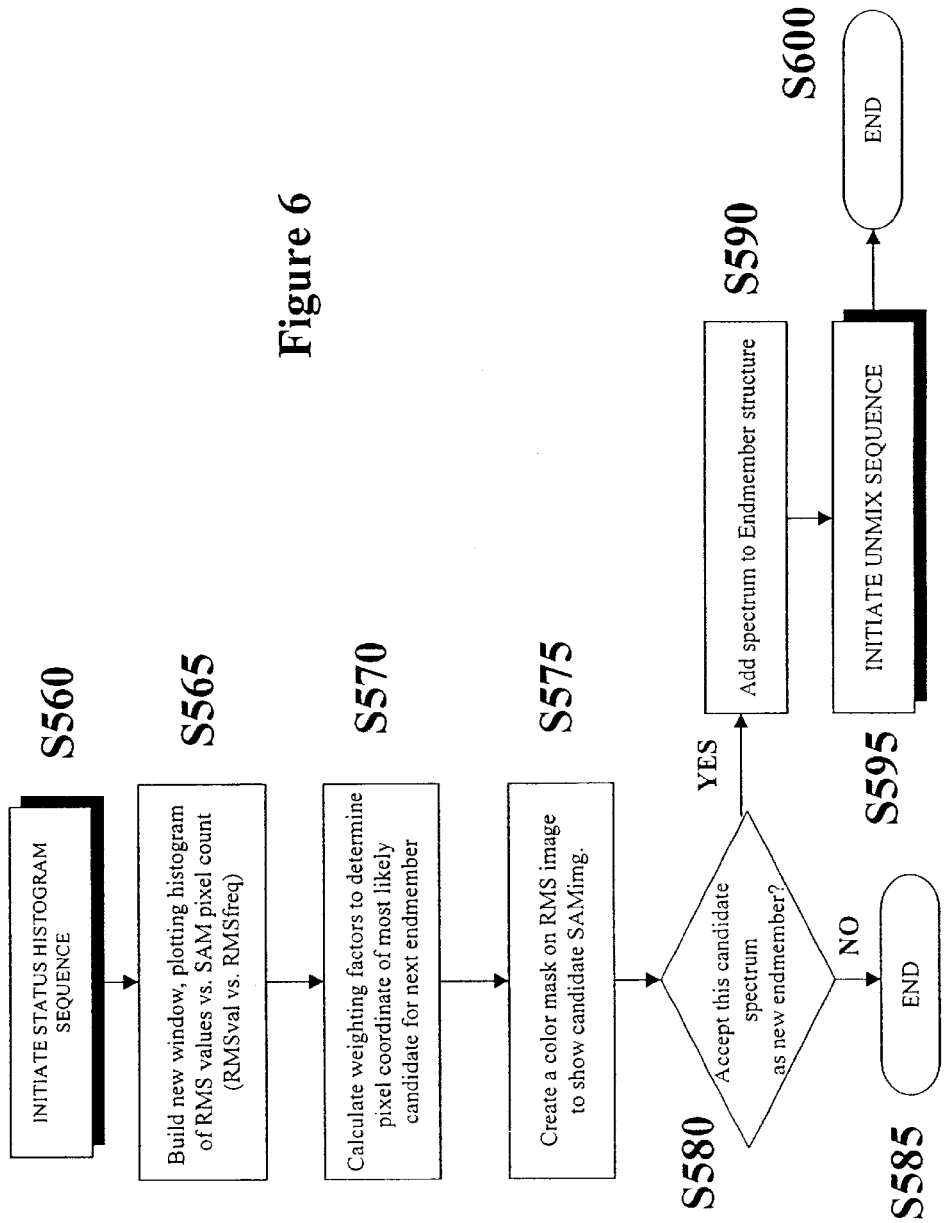
FIG. 6 is a flowchart for initiating a sequence for displaying status histograms according to an embodiment of the present invention.

Referring to FIG. 6, when x=500, a new display window is built which includes a plot of a histogram of RMS values versus SAM pixel count, i.e., RMSval vs. RMSfrequency S565. Weighting factors are calculated as follows to determine the pixel coordinate for the most likely endmember candidate S570. The factors are defined wherein RMSval ($K_x$) is the RMS error value for the corresponding pixel, RMSval(min) is the minimum RMS error value for the $K_x$ spectra, RMSval(max) is the maximum RMS error value for the $K_x$ spectra, RMSfreq($K_x$) is the value corresponding to the number of scene pixels that match the residual spectrum for the corresponding RMS error value, RMSfreq(min) is the number of occurrences of the least frequently occurring residual spectrum from the scene residual spectrum, and RMSfreq(max) is the number of occurrences of the most frequently occurring residual spectrum from the scene residual spectrum.

$$Normval(K_x) = \frac{RMSval(K_x) - RMSval(\min)}{RMSval(\max) - RMSval(\min)}$$

$$Normfreq(K_x) = \frac{RMSfreq(K_x) - RMSfreq(\min)}{RMSfreq(\max) - RMSfreq(\min)}$$

$$wgtfactor(K_x) = sqrt(Normval(K_x) * Normfreq(K_x))$$

$$candidate = MAX(wgtfactor)$$

The above-cited equations, or the like, act as a metric to determine the candidate endmember with the highest error and the largest frequency within the scene. After plotting the histogram and determining the best candidate endmember based on the weight factors, a color mask is created on an image of the scene in order to highlight for the user the pixels containing the candidate endmember S575. Using this color mapped image, the user can determine based on, among other things, spatial coherence, whether this candidate endmember is acceptable S580. If the candidate endmember is not acceptable, the process ends S585. At this point, the user can for example, select the candidate endmember with the next highest weight factor or adjust the SAM threshold, in order to find new candidate endmembers. If the candidate endmember is acceptable, it is added to the endmember structure already containing shade and initial vegetation endmembers S590. Finally, using this new endmember with the two previous endmembers, the scene reflectance data is subjected to the unmixing sequence S370–S380 and the process ends S600. This process is iterated to find new endmembers.

In an alternative embodiment of the present invention, the first new acceptable candidate endmember replaces one of the original two endmembers and the unmixing sequence is run on the scene reflectance data with the two remaining endmembers, to find a new third endmember.

In an alternate embodiment of the present invention, the whole of the processes described herein are automated, wherein all user interactions, definitions, and decisions (including how many endmembers there are) are completely replaced with decision tree algorithms. In this automated embodiment, preferable ranges are iteratively selected by a processor based on pre-programmed decision trees.

The embodiments described herein are intended to be exemplary, and while including and describing the best mode of practicing, are not intended to limit the invention. Those skilled in the art appreciate the multiple variations to the embodiments described herein which fall within the scope of the invention.

We claim:

1. A process for determining at least one candidate spectral endmember that represents a group of N spectra comprising:

unmixing the group of N spectra to determine what portion, if any, of each of N spectra comprising the group of N spectra match at least one of at least a first and second spectrum, with the first and second spectrum representing at least a first and a second characteristic expected to be in the group of N spectra;

calculating a first metric value for each of the N spectra, wherein the first metric value accounts for a remaining portion of each of the N spectra not matching the at least first and second spectrum;

defining a metric value range, wherein the spectra having first metric values within the metric value range are defined as M spectra;

comparing each of the M spectra to each of the N spectra to determine the frequency with which each of the M spectra occurs within the N spectra; and calculating a second metric value for each of the M spectra, wherein the second metric value combines the frequency of occurrence of each of the M spectra within the N spectra with a first metric value for each of the M spectra, wherein the M spectra having the largest second metric value is the at least one candidate endmember.

2. The process according to claim 1, wherein the at least a first and a second spectra are selected from the group consisting of vegetation, shade, soil, and nonphotosynthetic vegetation.

3. A process for determining at least one candidate spectral endmember that represents a group of N spectra comprising:

unmixing the group of N spectra to determine what portion, if any, of each of N spectra comprising the group of N spectra match at least one of the at least a first and second spectrum, with the first and second spectrum representing at least a first and a second characteristic expected to be in the group of N spectra;

defining an error value for each of the N spectra, wherein the error value is the portion of each of the N spectra that does not match a combination of the at least a first and a second spectrum;

comparing the error value for each of the N spectra to a predetermined error value range, wherein spectra having error values within the predetermined error value range are defined as M spectra;

comparing each of the M spectra, beginning with the M spectra having the highest error value, to each of the N spectra, to determine the frequency with which each of the M spectra occurs within the N spectra; and calculating a metric for each of the M spectra, wherein the metric combines the frequency of occurrence of each of the M spectra within the N spectra with an error value for each of the M spectra, wherein the M spectra having the largest metric is the at least one candidate endmember.

4. The process according to claim 3, wherein the at least a first and a second spectrum are selected from the group consisting of vegetation, shade, soil, and nonphotosynthetic vegetation.

5. The process according to claim 3, herein each error value corresponds to a residual spectra and the residual spectra in combination form a residual spectrum of the N pixels.

6. The process according to claim 5, further comprising calculating a root mean square (RMS) error value for each of the N pixels by combining the error values for the residual spectrum.

7. The process according to claim 6, wherein the step of comparing the error value for each of the N spectra to a predetermined error value range, wherein spectra having error values within the predetermined error value range are defined as M spectra includes:

determining an acceptable range of deviation from the mean RMS error;

comparing each of the RMS error values for each of the N pixels to the acceptable range of deviation from the mean RMS error and keeping the M pixels that are within the acceptable range.

8. The process according to claim 7, wherein the step of calculating a metric for each of the M spectra includes solving the following equations, wherein $K_x$ represents each of the M spectra, from x=1 to x= an upper limit, RMSval($K_x$) is the RMS error value for the corresponding M pixel, RMSval(min) is the minimum RMS error value for the M spectra, RMSval(max) is the maximum RMS error value for the M spectra, RMSfreq($K_x$) is the value corresponding to the number of N pixels that match the residual spectrum for the corresponding RMS error value for the M pixel, RMSfreq(min) is the number of occurrences of the least frequently occurring residual spectrum from the M pixel residual spectra, and RMSfreq(max) is the number of occurrences of the most frequently occurring residual spectrum from the M pixel residual spectra, Normval($K_x$)=(RMSval($K_x$)−RMSval(min))/(RMSval(max)−RMSval(min)) Normfreq($K_x$)=(RMSfreq($K_x$)−RMSfreq(min))/(RMSfreq(max)−RMSfreq(min)) wgtfactor($K_x$)=sqrt(Normval($K_x$)* Normfreq($K_x$)).

9. A process for determining at least one candidate spectral endmember within a scene having N pixels using scene spectral data comprising:
    unmixing the N pixels in the scene to determine what portions of each of the N pixels match at least one of a first endmember representing a first spectral characteristic expected to be in the scene and a second endmember representing a second spectral characteristic expected to be in the scene;
    defining a remaining portion for each of the N pixels not matching a combination of the first and second endmembers as an error value, wherein each error value corresponds to a residual spectra and the residual spectra in combination form a residual spectrum of the N pixels;
    calculating a root mean square (RMS) error for the N pixels by combining the error values for the residual spectra;
    determining an acceptable range of deviation from the mean RMS error;
    comparing each of the RMS error values for each of the N pixels to the acceptable range of deviation from the mean RMS error and keeping the M pixels that are within the acceptable range of deviation;
    comparing the corresponding residual spectra of the M pixels to the residual spectrum comprising the residual spectrum for the N pixels, to determine the frequency with which each of the corresponding residual spectra of the M pixels occurs within the residual spectra for the N pixels; and
    calculating a weighting factor for each of the M pixels, wherein the M pixel having the largest weighting factor is the at least one candidate endmember.

10. The process according to claim 9, wherein the first endmember is a shade endmember and further wherein the shade endmember is determined by a pre-selected baseline percentage of reflectance.

11. The process according to claim 10, wherein the second endmember is selected from the group consisting of a vegetation endmember, a soil endmember and a nonphotosynthetic vegetation endmember, with the vegetation endmember being determined by comparing scene spectral data for the N pixels to a known set of vegetation spectra, the soil endmember being determined by comparing scene spectral data for the N pixels to a known set of soil spectra, and the nonphotosynthetic vegetation spectra being determined by comparing scene spectral data for the N pixels to a known set of nonphotosynthetic vegetation spectra.

12. The process according to claim 11, wherein the step of comparing the scene spectral data for the N pixels to a known spectral data utilizes at least one spectral mapping algorithm.

13. The process according to claim 9, wherein the number of M pixels is at most 500.

14. The process according to claim 9, wherein the step of calculating a weighting factor for each of the number of M pixels includes solving the following equations, wherein $K_x$ represents each of the number of M pixels, from x=1 to x= an upper limit, RMSval($K_x$) is the RMS error value for the corresponding M pixel, RMSval(min) is the minimum RMS error value for the M spectra, RMSval(max) is the maximum RMS error value for the M spectra, RMSfreq($K_x$) is the value corresponding to the number of N pixels that match the residual spectrum for the corresponding RMS error value for the M pixel, RMSfreq(min) is the number of occurrences of the least frequently occurring residual spectrum from the N pixel residual spectra, and RMSfreq(max) is the number of occurrences of the most frequently occurring residual spectrum from the N pixel residual spectra, Normval($K_x$)=(RMSval($K_x$)−RMSval(min))/(RMSval(max)−RMSval(min)) Normfreq($K_x$)=(RMSfreq($K_x$)−RMSfreq(min))/(RMSfreq(max)−RMSfreq(min)) wgtfactor($K_x$)=sqrt(Normval($K_x$)* Normfreq($K_x$)).

15. The process according to claim 9, the step of comparing the corresponding residual spectrum of the M pixels to the residual spectra for the N pixels, to determine the frequency with which each of the corresponding residual spectra of the M pixels occurs within the residual spectrum for the N pixels utilizes at least one spectral matching algorithm.

16. The process according to claim 9, further comprising applying a shade mask to the unmixed pixels, such that only those of the N pixels not masked out are subject to the calculation of a root mean square error step.

17. The process according to claim 16, wherein the shade mask masks out the unmixed pixels comprised of greater than 80 percent shade.

18. The process according to claim 9, wherein the pre-selected baseline percentage of reflectance is at most 1 percent.

19. The process according to claim 9, wherein the scene spectral data is selected from the group consisting of hyperspectral data, multispectral data, and ultraspectral data.

20. The process according to claim 9, wherein the unmixing is linear.

21. The process according to claim 9, wherein the unmixing is non-linear.

* * * * *